| United States Patent [19] | [11] Patent Number: 4,853,487 |
|---|---|
| Nonn | [45] Date of Patent: Aug. 1, 1989 |

[54] PROCESS FOR THE PREPARATION OF HYDROXYBIPHENYLS

[75] Inventor: Alain Nonn, Saint Foy Les Lyon, France

[73] Assignee: Rhone-Poulenc Chimie, Courbevoie, France

[21] Appl. No.: 146,108

[22] Filed: Jan. 20, 1988

[30] Foreign Application Priority Data

Jan. 21, 1987 [FR] France ................................. 87 00824

[51] Int. Cl.$^4$ ............................................. C07C 39/14
[52] U.S. Cl. ................................................... 568/730
[58] Field of Search ......................... 568/722, 723, 730

[56] References Cited

U.S. PATENT DOCUMENTS

| 3,413,341 | 11/1968 | Bursach et al. | 568/730 |
|---|---|---|---|
| 3,752,878 | 8/1973 | Kehl et al. | 423/263 |
| 4,094,913 | 6/1978 | Carlson | 568/778 |
| 4,340,768 | 7/1982 | Jinbo et al. | 568/730 |
| 4,475,000 | 10/1984 | Pendery et al. | 568/730 |
| 4,490,564 | 12/1984 | Pendery | 568/730 |

FOREIGN PATENT DOCUMENTS

| 2376836 | 8/1978 | France . | |
|---|---|---|---|
| 69-17372 | 7/1969 | Japan . | |
| 22347 | 2/1979 | Japan | 568/730 |
| 5422347 | 2/1979 | Japan . | |
| 1235126 | 6/1971 | United Kingdom | 568/746 |

OTHER PUBLICATIONS

French Search Report for FR 87/00824 (2 pages).
Chemical Abstracts, vol. 90, No. 23, p. 629, No. 186584e (Jun. 4, 1979).

*Primary Examiner*—Werren B. Lone
*Attorney, Agent, or Firm*—Finnegan, Henderson, Farabow, Garrett & Dunner

[57] ABSTRACT

A process for the production of a hydroxybiphenyl by the hydrolysis of a bromobiphenyl, at a temperature below 300° C., in the presence of both a copper-based catalyst and a separate cocatalyst selected from amongst halides, phosphates, nitrates, alcoholates, silicates, alcohols, carboxylic acids, sulfonic acids, organic sulfur-containing compounds, carbon monoxide, quinolines, tertiary amines, ammoniums, phosphines, phosphoniums, cyanides and palladium.

14 Claims, No Drawings

PROCESS FOR THE PREPARATION OF HYDROXYBIPHENYLS

FIELD OF THE INVENTION

The present invention relates to a process for the production of hydroxybiphenyls. More specifically, it relates to a process for the preparation of 4,4'-dihydroxybiphenyl.

BACKGROUND OF THE INVENTION

Indeed, 4,4'-dihydroxybiphenyl is an intermediate which is currently sought in the industry of synthetic materials such as polyesters, polyepoxides and polyurethanes, as an antioxidant in resins or in the dyestuff industry.

The preparation of hydroxybiphenyls by the hydrolysis of halobiphenyls using a copper catalyst, such as, for example, copper sulfate (according to U.S. Pat. No. 4,475,000) or copper oxide (according to U.S. Pat. No. 4,340,768) in an aqueous basic medium is known.

Many processes for the preparation of hydroxyaryl compounds, which are carried out in the gaseous phase, i.e. at a temperature above 300° C., in the presence of a copper-based catalyst and a rare earth phosphate-based catalyst are also known. Thus, a process for the preparation of hydroxyaryl compounds, the aryl group of which contains one or more benzene rings, starting with equivalent halogenated compounds, by hydrolysis in the presence of a catalyst based on lanthanum phosphate or cerium phosphate and copper, which are jointly precipitated in the form of an inorganic polyphosphate, is described in U.S. Pat. No. 3,752,878. This reaction is carried out as a two-phase reaction, the catalyst being in the solid form, and the halogenated compound to be hydrolyzed being in the gaseous form, because the reaction is carried out at temperatures above about 300° C. The degree of conversion of the starting compound is low and the reaction conditions are too severe for them to be employed on an industrial scale.

The hydrolysis monocyclic aromatic halides at a lower temperature is shown in an abstract of Japanese Pat. No. 69/17372, in which the hydrolysis is carried out at approximately 200° C., in the presence of copper derivatives having the oxidation state two, such as copper sulfate, copper dibromide and copper diacetate. The duration of the hydrolysis reaction is particularly long, and sometimes reaches 10 hours for a yield not exceeding 25%. Therefore, this method cannot be adopted on an industrial scale.

Thus, for many years the industry has been in search of a process for the preparation of hydroxybiphenyls starting with halobiphenyls, which process is economically profitable and not dangerous.

DESCRIPTION OF THE INVENTION

The present invention has enabled this object to be achieved. The subject of the present invention is a process, suitable for industrial application, for the preparation of hydroxybiphenyls, wherein a bromobiphenyl of formula (I):

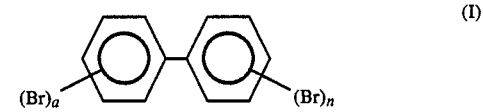

in which m and n are identical or different integers equal to 0, 1, 2 or 3, and the sum n+m of which is greater than or equal to 1 and less than or equal to 4, is brought into contact, in an aqueous liquid phase, at a temperature below 300° C., with a base of the formula $M(OH)_p$ in which M is a metal chosen from amongst alkali metals or alkaline earth metals, p is an integer equal to 1 or 2 depending on the valency of M, in the presence of both a copper-based catalyst and a separate cocatalyst chosen from amongst: halides (particularly, fluorides and bromides), phosphates, nitrates, alcoholates, inorganic or organic silicates or a source of inorganic or organic silicates, alcohols (particularly, methanol), carboxylic acids, sulfonic acids, organic sulfur-containing compounds, carbon monoxide or a source of carbon monoxide, quinolines, tertiary amines (including triethylamine and pyridines), quaternary ammoniums, phosphines, phosphoniums, cyanides and palladium.

It has been discovered that the use of a cocatalyst can advantageously facilitate the use of a more concentrated solution of base at a lower reaction temperature. Alternatively, with less concentrated solutions of base, even lower temperatures can be employed. Use of a cocatalyst can also facilitate the use of a lower weight ratio of catalyst to bromobiphenyl starting material, while obtaining the same yield.

The term "source of", as used in the context of this invention, may encompass those compounds which degrade in situ to form the desired cocatalyst.

The brominated derivatives may be prepared in a manner known to those skilled in the art, by the action of bromine on a biphenyl at ambient temperature for a few hours. Varying the temperature, the duration, the choice of solvent and the choice of certain bromination catalysts enables one or more bromine atoms to be attached.

Among derivatives of formula (I), derivatives in which n+m is equal to 1 to 2 are preferred. More preferred still are those in which n+m is equal to 2, most preferentially 4,4'-dibromobiphenyl.

Among bases of formula $M(OH)_p$, the use of strong alkali metal bases, and very particularly sodium hydroxide or potassium hydroxide, is preferred.

Representative copper-based catalysts include copper metal, copper having an oxidation state of one, such as cuprous oxide, halides, acetate, cyanide, thiocyanate, trifluoromethane sulfonic salt and cuprous sulfide, as well as copper derivatives having an oxidation state of two, such as cupric oxide, halides, acetates, acetylacetonates, metaborate, isobutyrate, citrate, cyclohexylbutyrate, dimethyldithiocarbamate, hexanoate, gluconate, hydroxide, oxalate, propionate, stearate, sulfate and trifluoroacetylacetonate.

However, it is preferable to employ copper oxides or halides having an oxidation state of one or two.

Representative cocatalysts which can enable either the temperature or the duration of the reaction to be reduced include halides, phosphates, nitrates or silicates. These compounds, when used, may be combined with protons or with cations of alkali metals, alkaline earth metals, or other metals (for example, copper or silver) or organic cations. Silicates may also be prepared in situ in the reaction medium by the action, for example, of a strong base on silica or on glass. Inorganic phosphates may also be prepared in situ starting with organic phosphates.

Representative cocatalysts which are completely organic may include alcoholates and alcohols preferably containing 1 to 12 atoms, carboxylic acids containing 2 to 12 carbon atoms, sulfonic acids, for example benzene- or pyridinesulfonic acid, tertiary amines and ammoniums, phosphines and phosphoniums, quinolines and sulfur-containing compounds. Carbon monoxide, or a source of carbon monoxide (including organic sources, such as formates), may also be mentioned.

Examples of cocatalysts of the present invention include diphenyl sulfide, dithiophene, potassium fluoride and/or sodium fluoride, phosphoric acid, nitric acid, sodium methylate, methyl formate, glasses, for example Pyrex, silica, methyl orthoformate, methanol, 8-hydroxyquinoline-4-sulfonic acid, tetrabutylammonium bromide, triethylamine, pyridine, pyridinesulfonic acid, benzenesulfonic acid, tetraphenylphosphonium chloride, triphenylphosphine, trisulfonated triphenylphosphine, triphenylphosphine oxide, tributylphosphine, tricyclohexylphosphine, chromium hexacarbonyl, palladium foam and N-methylpyrrolidone.

The use of fluorides, bromides, phosphates, nitrates, formates, such as organic formates, or alkali metal silicates is preferred.

With respect to reaction conditions, temperature is important from an economic standpoint. To optimize the economics, the temperature employed should be less than 300° C., and is preferably from 210° to 250° C., more preferably from 220° to 250° C. The pressure employed may be the self-generated pressure obtained at the reaction temperature by the vaporization of the compounds present. Pressure may be increased by any inert solvent such as nitrogen or any gas which does not react with the reaction compounds. As the reaction is carried out in an aqueous medium, it is preferable to employ a mono- or polybromobiphenyl at a concentration greater than 0.15 mole per liter of water, and preferably from 0.15 to 2 moles per liter of water. It is preferable to employ a quantity of a base of the formula $M(OH)_p$ which releases at least 2 equivalents of hydroxyl per atom of bromine to be hydrolyzed, and which has a concentration in water ranging from one mole equivalent per liter to ten mole equivalents per liter, more preferably, ranging from five mole equivalents per liter to ten mole equivalents per liter.

The gravimetric quantity of the copper-based catalyst is preferably from 0.2% to 5% relative to the quantity of bromobiphenyl introduced.

The molar quantity of the cocatalyst is preferably from about 0.1 to 200 times the molar quantity of the catalyst. A highly excessive quantity would not be deleterious to the process of the invention; however, it does not offer any additional advantage. The effective quantity will simply be adapted by the person skilled in the art to the profitability of the process.

The invention enables hydroxybiphenyls to be prepared, such as 4-hydroxybiphenyl, 2-hydroxybiphenyl, 3-hydroxybiphenyl, 4,4'-dihydroxybiphenyl, 2,2'-dihydroxybiphenyl, 2,4'-dihydroxybiphenyl, 2,4,4'-trihydroxybiphenyl and tetrahydroxybiphenyls.

Preferably, the reaction medium has a pH ranging from 5 to 10.

The following examples illustrate certain embodiments of the invention and should not be regarded as limiting the scope or spirit of the invention.

EXAMPLES 1 to 16

The following compounds were introduced into a 75 ml Hastelloy C 276 reactor:

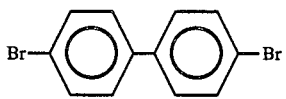

| | |
|---|---|
| | 2 g (6.4 mmoles) |
| $Cu_2O$ | 10 mg (0.07 mmoles) |
| 5N NaOH in $H_2O$ | 20 ml (100 mmoles) |
| Cocatalyst | 2 moles per mole of $Cu_2O$ or 20 mg in the case of Pyrex. (The gases were introduced by purging). |

After purging once with argon, closing the autoclave, and thereafter optionally introducing the gaseous cocatalyst, the autoclave was placed in an oven which was equipped for agitation and heated to 250° C. After a reaction time T, the reactor was cooled to ambient temperature. The reaction mixture was diluted with 20 ml of water (rinsing the reactor), acidified with 25 ml of 4N sulfuric acid and extracted with methyl isobutyl ketone ($1 \times 20$ ml + $5 \times 10$ ml). The organic phase was dried over sodium sulfate. The yields were determined by high performance liquid chromatography.

Table I, as follows, shows the results obtained.

TABLE 1

| No. | Cocatalysts | Duration | Yield (%) 4-OH | Yield (%) 4,4'-di-OH |
|---|---|---|---|---|
| 1* | — | 3 h | 0.4 | 52.9 |
| 2* | — | 5 h | 1.5 | 85.2 |
| 3* | — | 7 h | 1.3 | 90.5 |
| 4 | $Ph_2S$ | 3 h | 0.5 | 60.6 |
| 5 | Dithiophene | 3 h | 0.6 | 68.8 |
| 6 | KF | 3 h | 1.7 | 88.8 |
| 7 | NaF | 3 h | 1.4 | 93.3 |
| 8 | $H_3PO_4$ | 3 h | 2.7 | 91.2 |
| 9 | $HNO_3$ | 3 h | 1.2 | 83.6 |
| 10 | NaCN | 3 h | 0.3 | 58.9 |
| 11 | NaOMe | 3 h | 4.2 | 83.0 |
| 12 | NaBr (1 mole per mole of $Br_2$ $(C_6H_4)_2$) | 3 h | 1.2 | 84.5 |
| 13 | $HCO_2Me$ | 3 h | 1.7 | 90.4 |
| 14 | 6.4% CO in $N_2$ (1 purging) | 3 h | 0.5 | 62.5 |
| 15 | Pyrex | 3 h | 1.7 | 86.9 |
| 16 | $SiO_2$ | 3 h | 1.8 | 89.4 |

*Comparative Examples

EXAMPLE 17

The reaction was carried out as described in Example 1, introducing:
2 g of 4,4'-dibromobiphenyl: (6.4 mmoles)
20 ml of 5N NaOH in $H_2O$: (100 mmoles)
10 mg of cuprous oxide: (0.07 mmoles)
1.4 g of NaBr: (14 mmoles)

After 3 hours of reaction, a 4,4'-dihydroxybiphenyl yield of 84.7% and a 4-hydroxybiphenyl yield of 1.2% are obtained.

EXAMPLE 18

The reaction was carried out as described in Example 1, hydrolyzing a mixture of:

2-bromobiphenyl
2,4-dibromobiphenyl
2,4'-dibromobiphenyl
2,2'-dibromobiphenyl
2,4,4'-tribromobiphenyl
obtained by the bromination of 2-bromobiphenyl with bromine in dichloromethane, in the presence of 1% of ferric chloride, for 48 hours.

The hydrolysis was carried out in the presence of 0.07 mole of cuprous oxide and 2 moles of silica per mole of catalyst, at 250° C., in 5N sodium hydroxide in $H_2O$.

After 3 hours, a mixture consisting of the following was obtained:
2-hydroxybiphenyl
2,4-dihydroxybiphenyl
2,4'-dihydroxybiphenyl
2,2'-dihydroxybiphenyl
2,4,4'-trihydroxybiphenyl The products were identified by nuclear magnetic resonance spectroscopy after isolating by preparative gas chromatography.

EXAMPLE 19

The following experiments were carried out under the same conditions as in Examples 1 to 16, using:
2 g of 4,4'-dibromobiphenyl
100 mg of cuprous oxide
20 ml of 5N NaOH in $H_2O$
at 230° C., using, as indicated in Table 2, butanol as cocatalyst.

TABLE 2

| No. | Cocatalyst | Duration | Yield (%) 4-OH | Yield (%) 4,4'-di-OH |
|---|---|---|---|---|
| 1* | — | 7 h 30 | traces | 69.0 |
| 2 | 10 ml BuOH | 7 h 30 | 1.8 | 84.0 |

*Comparative Example

EXAMPLES 20 TO 37

The experiments were carried out strictly under the conditions of Example 1, using:
2 g of 4,4'-dibromobiphenyl,
10 mg of cuprous oxide,
20 ml of 5N NaOH in $H_2O$,
2 moles of cocatalyst per mole of $Cu_2O$.

| No. | Cocatalysts | Yield (%) 4-OH | Yield (%) 4,4'-di-OH |
|---|---|---|---|
| 20* | None | 0.4 | 58.1 |
| 21 | HC(OCH$_3$)$_3$ | 1.4 | 85.1 |
| 22 | CH$_3$OH | 1.9 | 87.0 |
| 23 | 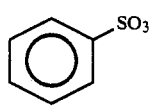 8-hydroxyquinoline-5-SO$_3$H | 1.9 | 90.3 |
| 24 | nBu$_4$NBr | 1.2 | 85.5 |
| 25 | Et$_3$N | 0.8 | 70.0 |
| 26 | Pyridine | 2.0 | 82.8 |
| 27 |  pyridine-SO$_3$H | 1.0 | 75.3 |
| 28 | 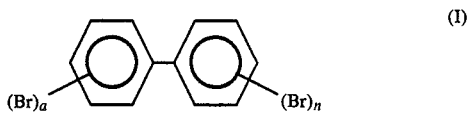 PhSO$_3$H | 1.6 | 85.7 |
| 29 | φ$_4$P Cl | 1.8 | 82.2 |
| 30 | φ$_3$P | 1.9 | 86.3 |
| 31 | TPPTS (HSO$_3$φ)$_3$P | 1.6 | 79.0 |
| 32 | φ$_3$P = 0 | 1.1 | 65.2 |
| 33 | nBu$_3$P | 2.3 | 88.8 |
| 34 | 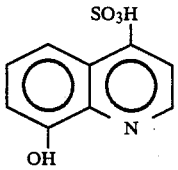 | 12.2 | 74.5 |
| 35 | Cr(CO)$_6$ | 2.3 | 85.7 |
| 36 | Pd (foam) | 1.7 | 77.0 |
| 37 | 8-hydroxyquinoline | 1.4 | 90.3 |

*Comparative Example

Moreover, on adding 0.5 ml of N-methylpyrrolidone in experiment 20, under the same conditions, the following were obtained:

Yield (4—OH) = 2.5%

Yield (4,4'-di—OH) = 73.9%

We claim:

1. A process for the preparation of a hydroxybiphenyl, comprising the step of bringing a bromobiphenyl of formula (I):

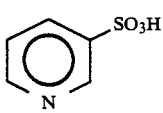

in which m and n are identical or different integers equal to 0, 1, 2 or 3, and the sum n+m of which is greater than or equal to 1 and less than or equal to 4, into contact with a base of the formula M(OH)$_p$ in which M is a metal chosen from amongst alkali metals or alkaline earth metals, and p is an integer equal to 1 or 2 depending on the valency of M, in an aqueous liquid phase, at a temperature below 300° C., and in the presence of both a copper-based catalyst and a separate cocatalyst selected from the group consisting of halides, phosphates, nitrates, alcoholates, inorganic or organic silicates or sources of inorganic or organic silicates, alcohols, carboxylic acids, sulfonic acids, organic sulfur-containing compounds, carbon monoxide or a source of carbon monoxide, quinolines, ammoniums, tertiary amines, phosphines, phosphoniums, cyanides and palladium.

2. The process of claim 1, wherein, in formula (I), n+m is equal to 1 or 2.

3. The process of claim 1, wherein said bromobiphenyl of formula (I) is 4,4'-dibromobiphenyl.

4. The process of claim 1, wherein said copper-based catalyst is chosen from amongst copper oxides or halides, the copper having an oxidation state of one or two.

5. The process of claim 1, wherein said cocatalyst is chosen from amongst fluorides, bromides, alkali metal phosphates, organic formates and alkali metal silicates.

6. The process of claim 5, wherein said alkali metal silicates are prepared in situ, starting with silica or glass.

7. The process of claim 1, wherein a reaction temperature from 220° to 250° C. is employed.

8. The process of claim 1, wherein said phosphates are selected from the group consisting of inorganic phosphates and organic sources of inorganic phosphates.

9. The process of claim 1, wherein said alcoholates are selected from the group consisting of alkali metal, alkaline earth metal, copper and silver alcoholates.

10. The process of claim 1, wherein said aqueous liquid phase has a pH ranging from 5 to 10.

11. The process of claim 1, wherein the base is at a concentration of at least 5N.

12. The process of claim 11, wherein the temperature ranges from about 220° to 250° C.

13. The process of claim 11, wherein said base is sodium hydroxide.

14. The process of claim 1, wherein the separate cocatalyst is a non-rare earth phosphate.

* * * * *